[19] United States Patent
Lemanski et al.

[11] 4,293,498
[45] Oct. 6, 1981

[54] PREPARATION OF MALEIC ANHYDRIDE

[75] Inventors: Michael F. Lemanski, Cleveland; Noel J. Bremer, Stow; Ernest C. Milberger, Solon, all of Ohio

[73] Assignee: Standard Oil Co., Cleveland, Ohio

[21] Appl. No.: 199,148

[22] Filed: Oct. 22, 1980

[51] Int. Cl.³ .......................................... C07D 307/60
[52] U.S. Cl. ................. 260/346.75; 252/437
[58] Field of Search .................................. 260/346.75

[56] References Cited

U.S. PATENT DOCUMENTS

| | | | |
|---|---|---|---|
| 3,156,707 | 11/1964 | Kerr | 260/346.75 |
| 3,864,280 | 2/1975 | Schneider | 252/435 |
| 3,915,892 | 10/1975 | Harrison | 252/435 |
| 3,931,046 | 1/1976 | Weinstein et al. | 252/429 R |
| 3,932,305 | 1/1976 | Jurewicz et al. | 252/429 R |
| 3,987,063 | 10/1976 | Lemal et al. | 260/346.75 |
| 4,002,650 | 1/1977 | Bremer et al. | 260/346.75 |
| 4,016,105 | 4/1977 | Kerr | 252/437 |
| 4,017,521 | 4/1977 | Schneider | 260/346.75 |
| 4,035,417 | 7/1977 | Izawa et al. | 260/530 N |
| 4,043,943 | 8/1977 | Schneider | 252/437 |
| 4,064,070 | 12/1977 | Harrison | 252/435 |
| 4,147,661 | 4/1979 | Higgins et al. | 252/435 |
| 4,149,992 | 4/1979 | Mount et al. | 252/435 |
| 4,179,404 | 12/1979 | Barone | 252/435 |
| 4,187,235 | 2/1980 | Katsumoto et al. | 260/346.75 |
| 4,244,879 | 1/1981 | Bremer et al. | 260/346.75 |

FOREIGN PATENT DOCUMENTS 3431 8/1979 European Pat. Off. .

OTHER PUBLICATIONS

Littler et al. J. of Chem. Soc. (1959) pp. 1299-1305.

Primary Examiner—Henry R. Jiles
Assistant Examiner—Bernard Dentz
Attorney, Agent, or Firm—Joseph G. Curatolo; Herbert D. Knudsen; Larry W. Evans

[57] ABSTRACT

The present invention provides a process for the preparation of oxidation catalysts containing mixed oxides of vanadium and phosphorus, which catalysts are particularly effective in the oxidation of n-butane, n-butenes, 1,3-butadiene or a mixture thereof with molecular oxygen or an oxygen-containing gas in the vapor phase to produce high yields of maleic anhydride with good selectivity. A vanadium compound is introduced into an olefinic halogenated organic liquid medium, a phosphorus-containing compound is added to the medium, reduction of at least a portion of the vanadium to a +4 valence state is effected either prior to or subsequent to the addition of the phosphorus-containing compound, and the resulting vanadium-phosphorus oxide catalyst precursor is recovered, dried and calcined.

10 Claims, No Drawings

PREPARATION OF MALEIC ANHYDRIDE

BACKGROUND OF THE INVENTION

This invention relates to a process for preparing catalysts useful in the production of dicarboxylic acid anhydrides by the oxidation of hydrocarbons. More particularly it is directed to the preparation of catalysts suitable for producing maleic anhydride from 4-carbon atom hydrocarbons, such as n-butane, n-butenes, 1,3 butadiene or a mixture thereof.

Catalysts containing vanadium and phosphorus oxides have been used in the oxidation of 4-carbon atom hydrocarbons, such as n-butane, n-butenes, 1,3 butadiene or mixtures thereof with molecular oxygen or an oxygen-containing gas to produce maleic anhydride. Conventional methods of preparing these catalysts involve combining a vanadium compound, a phosphorus compound, and if desired, promoter element compounds in a reducing medium under conditions which will provide vanadium in a valence state below +5 to form catalyst precursors capable of being converted to an oxide. The catalyst oxide precursor is then recovered and calcined to provide active catalytic material.

The use of gaseous HCl as a reducing agent for vanadium is disclosed in U.S. Pat. No. 4,002,650 where the vanadium and phosphorus components are present in an aqueous solution. The use of gaseous HCl as a reducing agent for vanadium is also described in U.S. Pat. Nos. 3,864,280; 4,017,521 and 4,043,943 where the vanadium and phosphorus components are reacted in a saturated organic liquid medium. The organic medium described particularly in U.S. Pat. No. 4,043,943, may include saturated, oxygen-containing halogenated organics and inert diluents including halogenated aromatics and hydrocarbons.

Similar preparational techniques are described in European Patent Appln. No. 3,431 in which the additional step of comminuting the vanadium-phosphorus precursor to a particle size of 500 to 700 microns (0.5 to 0.7 mm) is disclosed.

The use of such reducing agents as disclosed in the art, requires special precautions in the preparation of these catalysts because of the corrosive nature of the materials utilized.

U.S. Pat. No. 4,016,105 describes the preparation of vanadium and phosphorus oxide-containing catalysts utilizing as reducing agents organic acids including oxalic, citric, formic, ascorbic and malic, or aldehydes, including formaldehyde and acetaldehyde, together with a co-reducing secondary alcohol. These reducing agents are added to an aqueous solution containing the vanadium and phosphorus components.

A method for preparing catalysts containing vanadium and phosphorus oxides was described in U.S. Pat. Nos. 4,132,670 and 4,187,235 including forming a vanadium-containing compound dispersion in an organic liquid medium such as alcohols, aldehydes, ketones, ethers or mixtures thereof, heating the dispersion to reduce the vanadium, and thereafter adding phosphoric acid in an organic solvent. The organic medium may contain inert diluents, including chlorinated hydrocarbons. These patents teach that organic compounds satisfactory for use in the preparation of such oxides must not contain olefin double bonds.

U.S. Pat. Nos. 4,149,992 and 4,116,868 disclose the preparation of vanadium and phosphorus oxide-containing catalysts prepared from a pentavalent phosphorus-containing compound in a liquid reaction zone. The liquid reaction zone may include aromatic compounds such as benzyl chloride.

In the prior art, separation and recovery of the catalyst precursor from the reaction solution has provided difficulties. Where HCl gas is used as a reducing agent for a vanadium compound, containment and disposal of the excess, corrosive gas required constitutes a problem in commercial scale-up of the catalyst preparation. Conventionally, the solution containing the precursor must be evaporated down, usually to a catalyst precursor-containing paste which must then be dried, broken up and ground. This too provides difficulties for the commercial scale-up of the process, particularly where the catalyst precursor-containing solution includes flammable organic liquids.

SUMMARY OF THE INVENTION

It is therefore an object of the invention to provide a process for preparing vanadium and phosphorus-containing oxidation catalysts.

It is a further object of the invention to provide a process of preparing vanadium and phosphorus-containing catalysts useful for the oxidation of 4-carbon atom hydrocarbons to produce maleic anhydride, which catalysts exhibit high yields and selectivity to maleic anhydride.

It is a further object of the invention to provide a process of preparing vanadium and phosphorus-containing catalysts useful for the oxidation of 4-carbon atom hydrocarbons to produce maleic anhydride which utilizes mild reducing agents to effect an average valence state of about +3.5 to about +4.6 in the vanadium present in the catalyst.

It is a further object of the invention to provide a process of preparing vanadium and phosphorus-containing catalysts useful for the oxidation of 4-carbon atom hydrocarbons to produce maleic anhydride which is simplified, economical and avoids the hazards of corrosion and/or flammability, and is capable of commercial scale-up.

It is a further object of the invention to provide a process of preparing vanadium and phosphorus-containing catalysts useful for the oxidation of 4-carbon atom hydrocarbons to produce maleic anhydride which includes improved recovery of catalyst precursors from the reaction medium.

These and other objects, together with the advantages thereof over known methods, which shall be apparent from the specification which follows, are accomplished by the invention as hereinafter described and claimed.

In general the process of the present invention comprises the steps of (a) introducing a pentavalent vanadium-containing compound into an olefinic, halogenated organic liquid-containing liquid medium;

(b) effecting reduction of at least a portion of said vanadium to a valence state of +4;

(c) adding a phosphorus-containing compound to said medium to form a catalyst precursor precipitate;

(d) recovering the catalyst precursor precipitate;

(e) drying the catalyst precursor precipitate;

(f) calcining the catalyst precursor precipitate.

Another embodiment of the process of the present invention comprises the steps of (a) introducing a pentavalent vanadium compound and a phosphorus compound into an olefinic halogenated organic liquid-containing liquid medium;

(b) effecting reduction of at least a portion of the valence to a valence state of about +4 of the vanadium while in the presence of the phosphorus compound to form a vanadium-phosphorus mixed oxide precursor;

(c) recovering the vanadium phosphorus mixed oxide catalyst precursor;

(d) drying said catalyst precursor; and (e) calcining the catalyst precursor.

The catalysts prepared by the above process are particularly effective in the oxidation of 4-carbon atom hydrocarbons such as n-butane, n-butenes, 1,3 butadiene or mixtures thereof with molecular oxygen or an oxygen-containing gas in the vapor phase to produce high yields of maleic anhydride with high selectivity. Essentially all the product produced in this oxidation process is maleic anhydride, with only minor amounts of lower acids being detected.

DETAILED DESCRIPTION OF THE INVENTION

In the process for the preparation of an oxidation catalyst containing the mixed oxides of vanadium and phosphorus, a vanadium compound, particularly a pentavalent vanadium compound, is introduced into an olefinic, halogenated organic liquid medium. Suitable vanadium compounds containing pentavalent vanadium include: vanadium pentoxide or vanadium salts, such as ammonium metavanadate and vanadium oxytrihalides. Vanadium pentoxide is preferred.

We have discovered that olefinic, halogenated organic liquids, contrary to the teachings of the prior art, are suitable, mild reducing agents for vanadium, capable of reducing pentavalent vanadium to an average valence of between +3.5 and +4.6, that is, they are capable of reducing at least a portion of the pentavalent vanadium introduced into such a liquid to a +4 valence state. Such partial reduction of vanadium permits its use in the preparation of catalysts useful in the production of maleic anhydride from 4-carbon atom hydrocarbons. A harsher reducing agent would reduce the vanadium to a much lower valence state, possibly to base metal, in both cases, rendering the vanadium virtually inactive catalytically.

As used in this specification, the term "olefinic halogenated organic liquids" refers to compounds containing at least the elements carbon, hydrogen and a halogen, preferably chlorine and/or bromine, said compounds having at least one non-aromatic carbon to carbon double bond, and may include compounds having other functional groups provided that these functional groups do not adversely effect the formation of recoverable mixed oxides of vanadium and phosphorus, wherein said vanadium has an average valence of about +3.5 to about +4.6. These compounds must be liquid at some temperature within the range of temperatures between about 20° C. to about 150° C. It is preferred that the compound be high boiling, preferably boiling at about 150° C. or greater, and most preferably having a boiling point of about 200° C. or greater. Preferably, the olefinic, halogenated compound contains at least one halide atom attached to an allyl carbon atom. In the preferred embodiment of the invention, the olefinic halogenated organic liquids utilized do not contain an oxygen functionality.

The olefinic, halogenated organic liquids utilized act as solvents for phosphoric acid and are relatively unreactive towards phosphoric acid. These liquids are not, however, solvents for the mixed oxide of vanadium and phosphorus.

Suitable olefinic halogenated organic liquids for use in the invention include compounds such as perchloropropene, hexachlorobutadiene, hexachlorocyclopentadiene, and tetrabromoethylene. Preferred are perchloropropene and hexachlorobutadiene.

The liquid medium used in the process of the present invention may be comprised of substantially all olefinic halogenated organic liquids, or it may additionally include other organic reducing liquids for vanadium such as isobutanol, or non-reducing liquids for vanadium such as tert-butyl alcohol. The liquid medium used in the process of the present invention is preferably essentially anhydrous.

After the pentavalent vanadium compound is introduced into the liquid medium, reduction of the vanadium is effected either prior to or subsequent to the addition of a phosphorus-containing compound to the liquid medium. The reduction is effected preferably by heating the resulting reaction medium, with stirring if desired. Preferred vanadium and phosphorus oxide catalysts for the oxidation of 4-carbon atom hydrocarbons to maleic anhydride contain vanadium in an average valence state of about +3.5 to about +4.6. This average valence state is achieved when at least a portion of the pentavalent vanadium introduced into the reaction mixture is reduced to the +4 state. The average valence state of the vanadium is reduced preferably to about +4.1.

Suitable phosphorus compounds containing pentavalent phosphorus include: phosphoric acid, phosphorus pentoxide, or phosphorus perhalide, such as phosphorus pentachloride. Phosphoric acid and phosphorus pentoxide are preferred. The pentavalent phosphorus-containing compound is preferably added to the reaction medium in the form of a solution of the phosphorus-containing compound in either a component of the liquid reaction medium such as a halogenated olefinic organic liquid or isobutanol, or in a liquid capable of yielding the phosphorus-containing compound to the liquid reaction medium. After addition of the phosphorus-containing compound to the liquid reaction medium, it is preferable to heat the liquid reaction medium with stirring if necessary. The phosphorus-containing compound as described above, is added to the liquid medium (containing olefinic halogenated organic liquids) either before reduction of the pentavalent vanadium substantially occurs, or after such reduction.

The total $H_2O$ content of the liquid medium, is preferably below about 5%. The vanadium phosphorus mixed oxide catalyst precursor formed according to the process of the present invention forms fine granular particles, and is recovered from the liquid reaction medium by conventional methods including filtration, centrifugation and decantation.

The catalyst precursor or catalyst precursor precipitate is dried and calcined at a temperature of 250° C. to 600° C., preferably in the presence of an oxygen-containing gas.

It is within the scope of this invention, to include promoter element-containing compounds in the reaction mixture at a suitable point, either prior to or subsequent to reduction of the vanadium, in order that the catalyst precursor or catalyst precursor precipitate contain the promoter element. Suitable promoters include but are not limited to U, Co, Mo, Fe, Zn, Hf and Zr. Preferred are U and Co.

Catalysts prepared by this method may exhibit a phosphorus to vanadium ratio of about 0.5:1 to about 2:1. Preferred is a P/V ratio of about 0.9:1 to about 1.3:1. The ratio of the optional promoter element to vanadium may be 0:1 to about 1:1. When a promoter is to be included, it is preferably present in a ratio to vanadium of 0.05:1 to 0.5:1. The catalyst is activated by calcining it in air or an oxygen containing gas at a temperature of 250° C. to 600° C. for a period of up to 5 hours or more. Activation of the catalyst is accomplished by passing a mixture of steam and air or air alone over the catalyst at a temperature of about 300° C. to 500° C. for a period of about 1 to 5 hours.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen needed for the reaction to produce maleic anhydride is most conveniently added as air, by synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 2 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of 350° C. to 500° C. being preferred.

The catalyst may be used alone or a support could be employed. Suitable supports include silica, alumina, silica-alumina Alundum, silicon carbide, titania, boron phosphate, zirconia, and the like. The catalysts may be used in a fixed-bed reactor using tablets, pellets or the like, or in a fluid-bed reactor using catalysts preferably having a particle size of less than about 300 microns. The contact time may be as low as a fraction of a second or as high as 50 seconds. The reaction may be conducted at atmospheric, superatomspheric or subatmospheric pressure.

EXAMPLES 1 & 2

A catalyst of the formula $V_{1.0}P_{1.2}U_{0.2}O_x$ was prepared in the following manner. 45 grams vanadium pentoxide and 42.2 grams uranyl acetate dihydrate were added to 500 ml hexachlorobutadiene and were refluxed for about 16 hours. Acetic acid from the uranium-containing compound was distilled off, and reflux was continued for about 16 hours. 58.8 grams orthophosphoric acid were added to the mixture with reflux for about 16 hours during which 9 ml. water was collected from a Dean-Stark trap. The resulting mixture was filtered to yield a dark green catalyst precursor solid, which was washed in methylene chloride and dried at 100° C. The granular precursor was ground to less than 50 mesh (0.297 mm), mixed with 3 weight % graphite and pressed into 3/16 inch (0.48 cm) pellets. The pellets were calcined at 400° C., then ground and screened to 10-13 mesh (0.595-2.00 mm).

EXAMPLES 3-4

A catalyst of the formula $V_{1.0}P_{1.2}Co_{0.2}O_x$ was prepared according to the procedure set forth in examples 1 and 2 above, with the exception that the promoter metal containing compound used was cobaltous chloride hexahydrate.

The catalysts described in Examples 1-4 were used to produce maleic anhydride from butane using a 20 cc fixed-bed reactor consisting of a 38 cm length of stainless steel tubing having an outer diameter of about 1.3 cm and having a full length 0.31 cm axial thermowell. The reactor was heated with a split stainless steel block furnace. Flasks for receiving the product maleic anhydride were mounted in ice water, and tail gases were routed to a Carle Analytical Gas Chromatograph III for analysis. Reaction conditions and results of the tests run are described in Table I. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield} \times 100}{\text{Total Conversion}}$$

When the process of preparing catalysts containing mixed oxides of vanadium and phosphorus is employed according to the present invention, the hazards presented by using corrosive materials such as HCl gas are avoided. In addition, the vanadium and phosphorus-containing catalyst precursor can be separated from the reaction medium simply by filtration or similar methods, avoiding the hazards of evaporating off large quantities of flammable liquid. The liquid reaction medium produced by the process of the present invention, after the catalyst precursor has been removed, may easily be recycled for use in the reaction again.

As can be seen from the results listed in Table I, catalysts prepared according to the process of the invention, utilizing olefinic, halogenated organic liquids as the liquid medium or in the liquid medium for partially reducing vanadium, effect high yields and selectivities of 4-carbon atom hydrocarbons (such as butane) to maleic anhydride.

Thus it should be apparent to those skilled in the art that the subject invention accomplishes the objects set forth above. It is to be understood that the subject invention is not to be limited by the examples set forth herein. These have been provided merely to demonstrate operability, and the selection of vanadium and phosphorus-containing compounds, olefinic halogenated organic liquid-containing liquid media, promoter element-containing compounds if any, hydrocarbon feedstocks and reaction conditions can be determined from the total specification disclosure provided without departing from the spirit of the invention herein disclosed and described, the scope of the invention including modifications and variations that fall within the scope of the attached claims.

TABLE I

| | | | Preparation of Maleic Anhydride from n-Butane | | | | | | |
|---|---|---|---|---|---|---|---|---|---|
| | | Hours On | Temperature | | Air/HC | Contact | % | Maleic Anhydride | |
| Example | Catalyst | Stream | Bath (°C.) | Bed (°C.) | Ratio | Time (Sec.) | Conv. | % Selec. | % Yield |
| 1. | $V_{1.0}P_{1.2}U_{0.2}O_x$* | 168.0 | 501 | 508 | 64.5 | 1.5 | 90.8 | 41.7 | 37.9 |
| 2. | $V_{1.0}P_{1.2}U_{0.2}O_x$ | 308.0 | 426 | 431 | 60.0 | 1.7 | 63.6 | 57.6 | 36.6 |
| 3. | $V_{1.0}P_{1.2}Co_{0.2}O_x$ | 164.0 | 429 | 437 | 89.7 | 1.9 | 89.8 | 57.1 | 51.3 |
| 4. | $V_{1.0}P_{1.2}Co_{0.2}O_x$ | 179.2 | 430 | 437 | 90.8 | 1.9 | 89.3 | 55.6 | 49.7 |

*$x$ = number of oxygens needed to satisfy the valence requirements of the other elements.

We claim:
1. A process for the production of maleic anhydride by the oxidation of n-butane, n-butene, 1,3-butadiene or a mixture thereof with molecular oxygen or oxygen-containing gas in the vapor phase at a reaction temperature of 250° C.–600° C. in the presence of a catalyst containing the mixed oxides of vanadium and phosphorus, wherein said catalyst is prepared by
   (a) introducing a pentavalent vanadium-containing compound into an olefinic, halogenated organic liquid-containing liquid medium,
   (b) effecting reduction of at least a portion of said vanadium to a valence state of about +4;
   (c) adding a phosphorus-containing compound to said medium before or after effecting said reduction to form a catalyst precursor;
   (d) recovering the catalyst precursor;
   (e) drying the catalyst precursor;
   (f) calcining the catalyst precursor.
2. A process for the production of maleic anhydride by the oxidation of n-butane, n-butene, 1,3 butadiene or a mixture thereof with molecular oxygen or oxygen-containing gas in the vapor phase at a reaction temperature of 250° C.–600° C. in the presence of a catalyst containing the mixed oxides of vanadium and phosphorus prepared from at least one pentavalent vanadium-containing compound and at least one phosphorus-containing compound wherein the pentavalent vanadium is reduced an average valence state of about +3.5 to about +4.6, including the step of effecting reduction of at least a portion of the pentavalent vanadium to a valence state of +4 in an olefinic, halogenated organic liquid-containing liquid medium.

3. The process of claims 1 or 2 wherein said reduction of vanadium is effected in the presence of the phosphorus-containing compound.
4. A process as recited in claims 1 or 2 wherein said organic liquid medium is essentially anhydrous.
5. A process as recited in claims 1 or 2 wherein reduction of said vanadium is effected by heating the vanadium-containing liquid medium.
6. A process as recited in claims 1 or 2 wherein said organic liquid contains a chlorinated olefinic organic liquid.
7. A process as recited in claims 1 or 2 wherein said organic liquid contains a brominated olefinic organic liquid.
8. A process as recited in claims 1 or 2 wherein said olefinic, halogenated organic liquid is selected from hexachlorobutadiene, perchloropropene, hexachlorocyclopentadiene, tetrabromoethylene and mixtures thereof.
9. A process as recited in claims 1 or 2 wherein said oxidation catalyst is represented by the empirical formula $$V_1P_aM_bO_x$$

wherein M is selected from U, Co, Mo, Fe, Zn, Hf, Zr and mixtures thereof;
wherein a=0.5 to 2.0, b=0 to 1.0 and x is the number of oxygens required to satisfy the valence requirements of the other elements.
10. A process as recited in claims 1 or 2 wherein said organic liquid has a boiling point greater than about 150° C.

* * * * *